(12) United States Patent
Bearinger et al.

(10) Patent No.: US 9,469,871 B2
(45) Date of Patent: Oct. 18, 2016

(54) METHODS AND APPARATUS FOR POINT-OF-CARE NUCLEIC ACID AMPLIFICATION AND DETECTION

(71) Applicant: CORPOROS INC., Berwyn, PA (US)

(72) Inventors: Jane P. Bearinger, Berwyn, PA (US); Scott Castanon, Carlsbad, CA (US); Kenneth J. Michlitsch, Berwyn, PA (US)

(73) Assignee: CORPOROS INC., Berwyn, PA (US)

( * ) Notice: Subject to any disclaimer, the term of this patent is extended or adjusted under 35 U.S.C. 154(b) by 0 days.

(21) Appl. No.: 14/262,683

(22) Filed: Apr. 25, 2014

(65) Prior Publication Data

US 2014/0356874 A1 Dec. 4, 2014

Related U.S. Application Data

(63) Continuation-in-part of application No. 13/447,218, filed on Apr. 14, 2012, now Pat. No. 8,911,941.

(60) Provisional application No. 61/475,257, filed on Apr. 14, 2011, provisional application No. 61/818,891, filed on May 2, 2013, provisional application No. 61/894,392, filed on Oct. 22, 2013.

(51) Int. Cl.
*C12Q 1/68* (2006.01)
*B01L 3/00* (2006.01)
*B01L 7/00* (2006.01)

(52) U.S. Cl.
CPC ....... *C12Q 1/6844* (2013.01); *B01L 3/502715* (2013.01); *B01L 3/502723* (2013.01);
(Continued)

(58) Field of Classification Search
CPC ................ C12Q 1/6881; B01L 3/502715

USPC ................. 435/6.1, 91.2, 287.2; 422/501
See application file for complete search history.

(56) References Cited

U.S. PATENT DOCUMENTS

| 3,871,895 A | 3/1975 | Adler |
| 3,880,111 A | 4/1975 | Levine et al. |

(Continued)

FOREIGN PATENT DOCUMENTS

| EP | 1442787 A2 | 8/2004 |
| EP | 2258951 A1 | 12/2010 |

(Continued)

OTHER PUBLICATIONS

Bearinger et al.; Development and initial results of a low cost, disposable, point-of-care testing device for pathogen detection; IEEE Trans on Biomedical Engineering; 58(3); pp. 805-808; Mar. 2011.

(Continued)

*Primary Examiner* — Betty Forman
(74) *Attorney, Agent, or Firm* — Shay Glenn LLP

(57) ABSTRACT

Methods and apparatus are provided for point-of-care nucleic acid amplification and detection. One embodiment of the invention comprises a fully integrated, sample-to-answer molecular diagnostic instrument that optionally may be used in a multiplexed fashion to detect multiple target nucleic acid sequences of interest and that optionally may be configured for disposal after one-time use. The instrument preferable utilizes an isothermal nucleic acid amplification technique, such as loop-mediated isothermal amplification (LAMP), to reduce the instrumentation requirements associated with nucleic acid amplification. Detection of target amplification may be achieved, for example, via detection of a color shift or fluorescence in a dye added to the amplification reaction. Such detection may be performed visually by an operator or may be achieved utilizing an imaging technique, e.g., spectrophotometric imaging.

22 Claims, 15 Drawing Sheets

(52) U.S. Cl.
CPC ............ *B01L3/502738* (2013.01); *B01L 7/00* (2013.01); *C12Q 1/6825* (2013.01); *C12Q 1/6846* (2013.01); *B01L 2300/0861* (2013.01); *B01L 2300/18* (2013.01); *B01L 2400/06* (2013.01)

(56) References Cited

U.S. PATENT DOCUMENTS

| | | | |
|---|---|---|---|
| 5,356,595 | A | 10/1994 | Kanamori et al. |
| 5,411,876 | A | 5/1995 | Bloch et al. |
| 5,498,392 | A | 3/1996 | Wilding et al. |
| 5,753,186 | A | 5/1998 | Hanley et al. |
| 6,132,685 | A | 10/2000 | Kercso et al. |
| 6,162,400 | A | 12/2000 | Schembri |
| 6,326,083 | B1 | 12/2001 | Yang et al. |
| 6,379,929 | B1 | 4/2002 | Burns et al. |
| 6,452,625 | B1 | 9/2002 | Kapitza |
| 6,456,754 | B1 | 9/2002 | Augustsson |
| 6,594,075 | B1 | 7/2003 | Kanao et al. |
| 6,630,205 | B2 | 10/2003 | Brueck et al. |
| 6,723,290 | B1 | 4/2004 | Wardlaw |
| 6,866,823 | B2 | 3/2005 | Wardlaw |
| 7,348,969 | B2 | 3/2008 | Robrecht et al. |
| 7,391,053 | B2 | 6/2008 | Iizuka et al. |
| 7,435,578 | B2 | 10/2008 | Wikswo et al. |
| 7,452,726 | B2 | 11/2008 | Chou et al. |
| 7,466,409 | B2 | 12/2008 | Scherer et al. |
| 7,492,167 | B2 | 2/2009 | Reich et al. |
| 7,524,459 | B2 | 4/2009 | Adams et al. |
| 7,608,220 | B2 | 10/2009 | Jin et al. |
| 7,695,683 | B2 | 4/2010 | Quan et al. |
| 7,751,048 | B2 | 7/2010 | Yang et al. |
| 7,773,227 | B2 | 8/2010 | Yang et al. |
| 7,863,035 | B2 | 1/2011 | Clemens et al. |
| 7,868,665 | B2 | 1/2011 | Turner et al. |
| 8,105,849 | B2 | 1/2012 | Mcdevitt et al. |
| 8,270,071 | B2 | 9/2012 | Glaser et al. |
| 8,325,349 | B2 | 12/2012 | Cui et al. |
| 8,465,698 | B2 | 6/2013 | Yamakawa et al. |
| 8,538,120 | B2 | 9/2013 | Salsman et al. |
| 8,584,394 | B1 | 11/2013 | Thomas |
| 8,705,833 | B2 | 4/2014 | Yagi et al. |
| 8,717,556 | B2 | 5/2014 | Salsman |
| 8,794,050 | B2 | 8/2014 | Hutto et al. |
| 8,911,941 | B2 | 12/2014 | Michlitsch |
| 9,091,620 | B2 | 7/2015 | Yi |
| 2002/0081716 | A1 | 6/2002 | Yagi |
| 2003/0013109 | A1 | 1/2003 | Ballinger et al. |
| 2003/0138819 | A1* | 7/2003 | Gong ............... B01L 3/5027 435/6.11 |
| 2004/0115731 | A1 | 6/2004 | Hansen et al. |
| 2004/0151629 | A1* | 8/2004 | Pease ............... B01L 3/5027 422/68.1 |
| 2004/0165778 | A1 | 8/2004 | Cartlidge et al. |
| 2004/0191119 | A1 | 9/2004 | Zanzucchi et al. |
| 2005/0106713 | A1 | 5/2005 | Phan et al. |
| 2007/0003443 | A1* | 1/2007 | Sandell ............... B01L 3/0275 422/400 |
| 2007/0141605 | A1 | 6/2007 | Vann et al. |
| 2007/0292858 | A1 | 12/2007 | Chen et al. |
| 2007/0292941 | A1* | 12/2007 | Handique ............ B01L 3/5027 435/288.7 |
| 2008/0176755 | A1 | 7/2008 | Amundson et al. |
| 2008/0280285 | A1 | 11/2008 | Chen et al. |
| 2009/0130745 | A1 | 5/2009 | Williams et al. |
| 2009/0147918 | A1 | 6/2009 | Fowler et al. |
| 2009/0148933 | A1* | 6/2009 | Battrell ............... B01F 11/0071 435/287.2 |
| 2009/0325276 | A1 | 12/2009 | Battrell et al. |
| 2010/0015621 | A1 | 1/2010 | Chang et al. |
| 2010/0054574 | A1 | 3/2010 | Marcelpoil et al. |
| 2010/0079408 | A1 | 4/2010 | Leong et al. |
| 2010/0186524 | A1 | 7/2010 | Ariessohn et al. |
| 2011/0150705 | A1 | 6/2011 | Doyle et al. |
| 2011/0181884 | A1 | 7/2011 | Cui et al. |
| 2011/0223632 | A1 | 9/2011 | Yamada et al. |
| 2011/0234757 | A1 | 9/2011 | Zheng et al. |
| 2011/0294112 | A1 | 12/2011 | Bearinger et al. |
| 2011/0294199 | A1 | 12/2011 | Bearinger et al. |
| 2011/0311394 | A1 | 12/2011 | Worsman et al. |
| 2012/0008848 | A1 | 1/2012 | Beck |
| 2012/0044339 | A1 | 2/2012 | Stith et al. |
| 2012/0044341 | A1 | 2/2012 | Stith et al. |
| 2012/0045786 | A1 | 2/2012 | Stith |
| 2012/0045787 | A1 | 2/2012 | Boettiger |
| 2012/0112098 | A1 | 5/2012 | Hoyt |
| 2012/0202211 | A1 | 8/2012 | Ochoa Corona |
| 2012/0218379 | A1 | 8/2012 | Ozcan et al. |
| 2012/0250027 | A1 | 10/2012 | Zheng et al. |
| 2012/0329142 | A1 | 12/2012 | Battrell et al. |
| 2013/0078625 | A1 | 3/2013 | Holmes et al. |
| 2013/0273524 | A1 | 10/2013 | Ehrenkranz |
| 2013/0307954 | A1 | 11/2013 | Vaartstra |
| 2014/0267672 | A1 | 9/2014 | Morrison et al. |
| 2015/0035966 | A1 | 2/2015 | Salsman |
| 2015/0036131 | A1 | 2/2015 | Salsman |
| 2015/0037786 | A1 | 2/2015 | Salsman |
| 2015/0300957 | A1 | 10/2015 | Salsman |

FOREIGN PATENT DOCUMENTS

| | | |
|---|---|---|
| WO | WO2009/018473 A1 | 2/2009 |
| WO | WO2009/111573 A2 | 9/2009 |
| WO | WO2011/073410 A1 | 6/2011 |
| WO | WO2012/068499 A2 | 5/2012 |
| WO | WO2012/122379 A9 | 9/2012 |

OTHER PUBLICATIONS

Cui et al.; Lensless high-resolution on-chip optofluidic microscopes for Caenorhabditis elegans and cell imaging; PNAS; 105(31); pp. 10670-10675; Aug. 2008.

Cui et al.; Quantitative differential interference contrast microscopy based on structured-aperture interference; Applied Physics Letters; 93 (091113); 3 pgs.; Sep. 2008.

Good et al.; An effervescent reaction micropump for portable microfluidic systems; Lab on a Chip; Royal Society of Chemistry; 6(5); pp. 659-666; May 2006.

Hart et al.; Point-of-care oral-based diagnostics; Oral Diseases; 17(8); pp. 745-752; Nov. 2011.

Jacoby; Chromatograpy in the extreme; Chemical & Engineering News; 86(17); pp. 17-23; Apr. 28, 2008 (retrieved Nov. 9, 2015 from the Internet: http://cen.acs.org/articles/86/i17/Chromatography-Extreme.html: 5 pgs.).

Jangam et al.; Rapid, point-of-care extraction of himan immunodeficiency virus type 1 proviral DNA from whole blood for detection by real time PCR; Journal of Clinical Microbiology; 47(8); pp. 2363-2368; Aug. 2009.

LaBarre et al.; Non-instrumented nucleic acid amplification (NINA): Instrument free molecular malaria diagnostics for low-resource settings; 32nd Ann. Int. Conf. of the IEEE EMBS; Buenos Aires, Argentina; pp. 1097-1099; Aug. 31-Sep. 4, 2010.

Menassa et al.; Rapid detection of fungal keratitis with DNA-stabilizing FTA filter paper; Investigative Ophthalmology & Visual Science; 51(4); pp. 1905-1910; Apr. 2010.

Pang et al.; Fluorescence microscopy imaging with a Fresnel zone plate array based optofluidic microscope; Lab on a Chip; 11; pp. 36983702; Nov. 2011.

Poon et al.; Sensitive and inexpensive molecular test for falciparum malaria: Detecting plamodium falciparum DNA directly for heat-treated blood by loop-mediated isothermal amplification; Clinical Chemistry; 52(2); pp. 303-306; Dec. 2006.

Weigl et al.; Non-instrumented nucleic-acid amplification assay; Microfluidics; BioMEMS, and Medical Microsystems VI; Proc. of SPIE; 6886(04); San Jose, CA; 12 pgs.; Jan. 19, 2008.

Wu et al.; The application of Fresnel zone plate based projection in optofluidic microscopy; Opt. Express; 16(2); pp. 15595-15602; Sep. 2008.

Bearinger et al.; U.S. Appl. No. 14/941,170 entitled "Methods and apparatus for point-of-care nucleic acid amplfication and detection," filed Nov. 13, 2015.

* cited by examiner

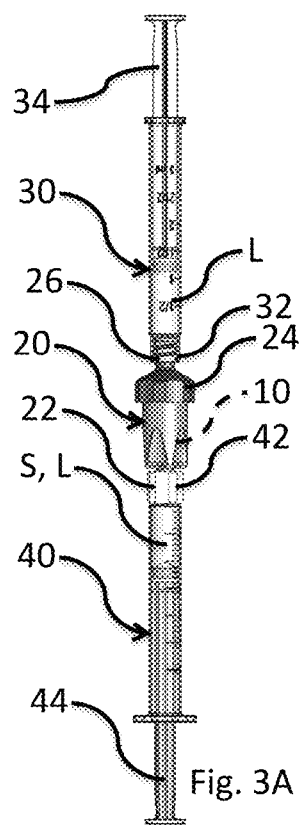
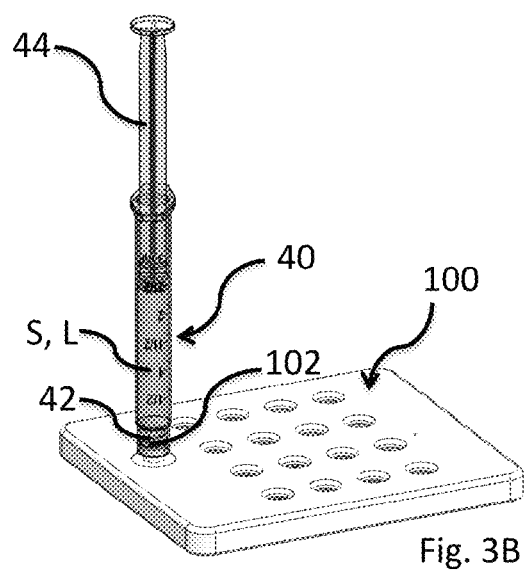
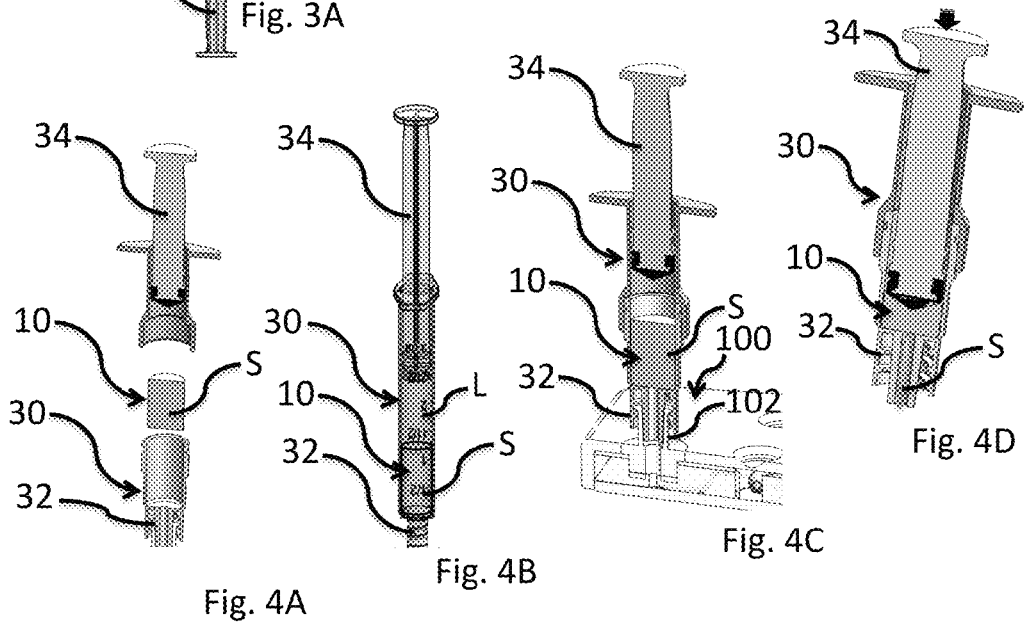

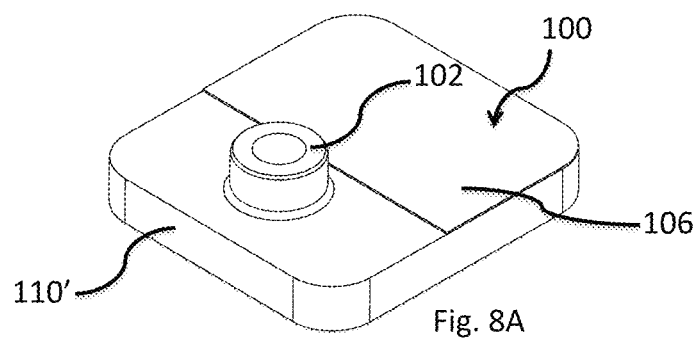
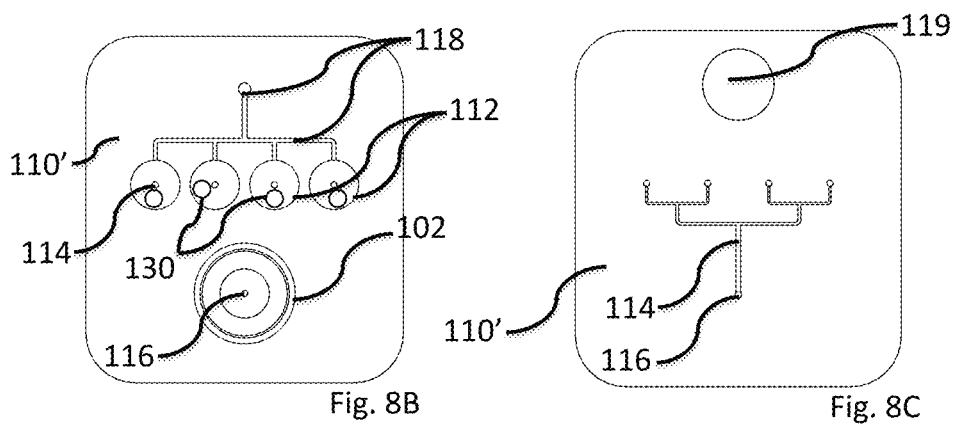
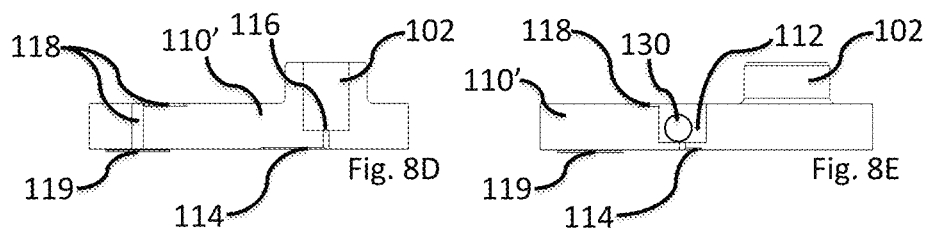

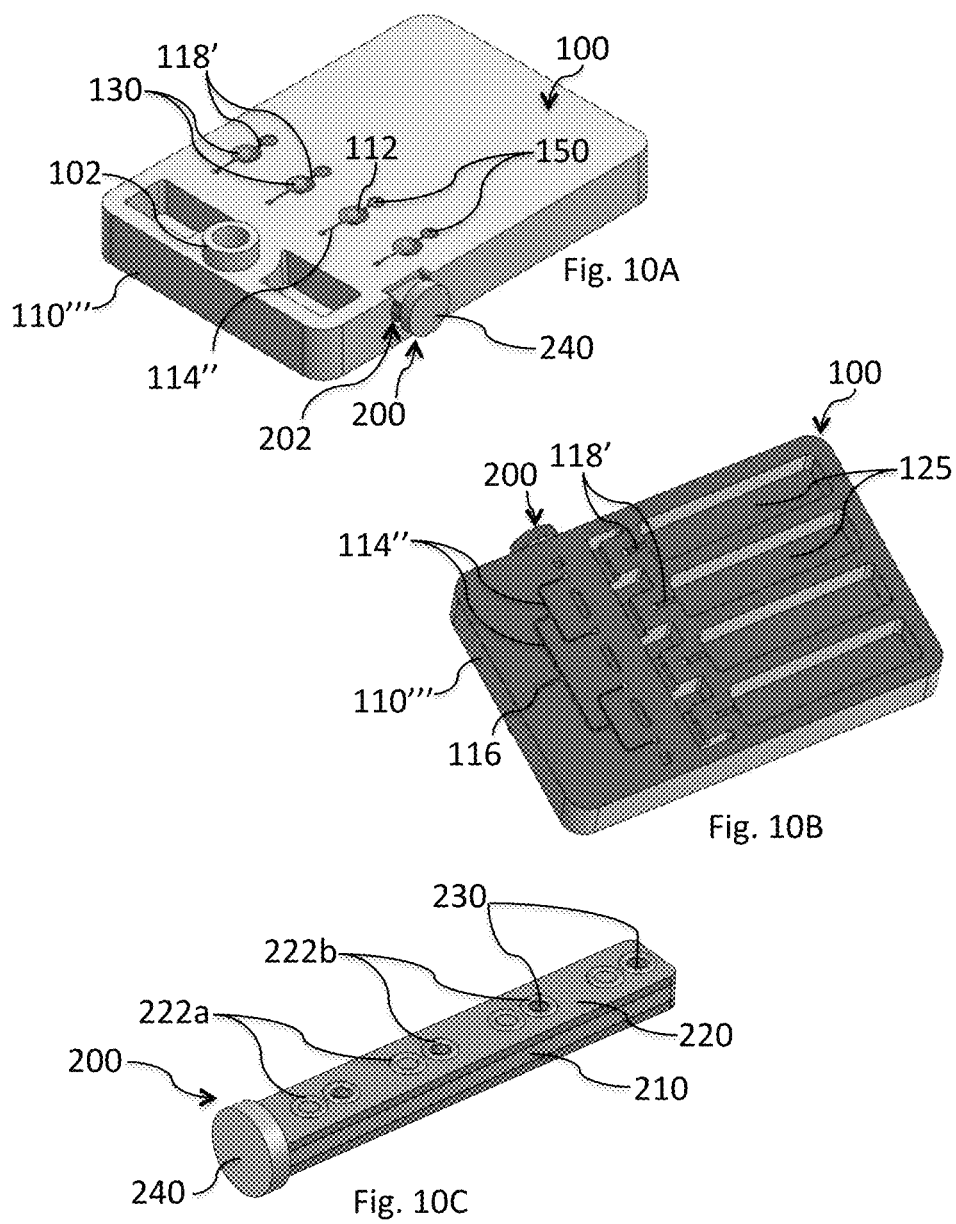

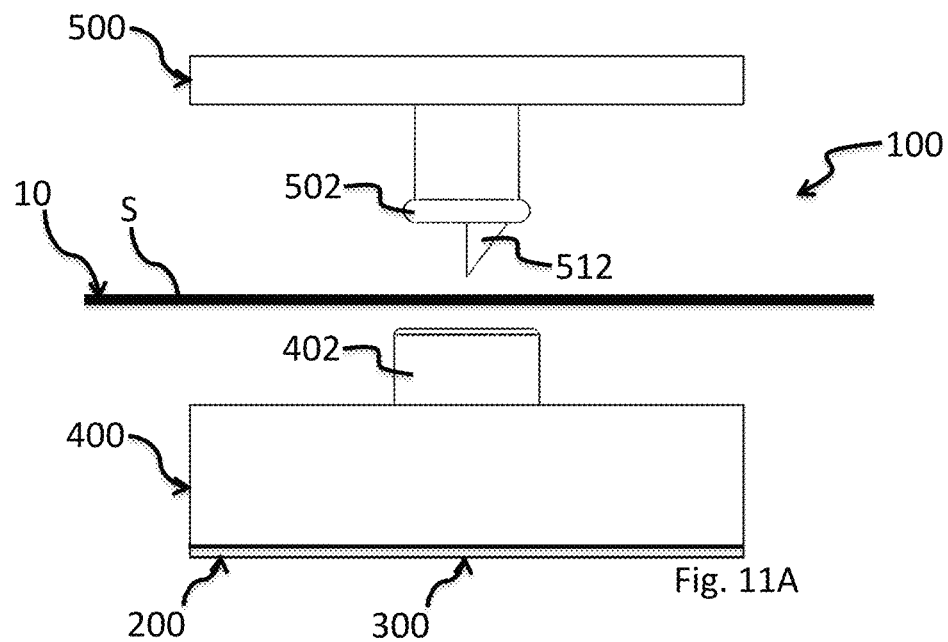
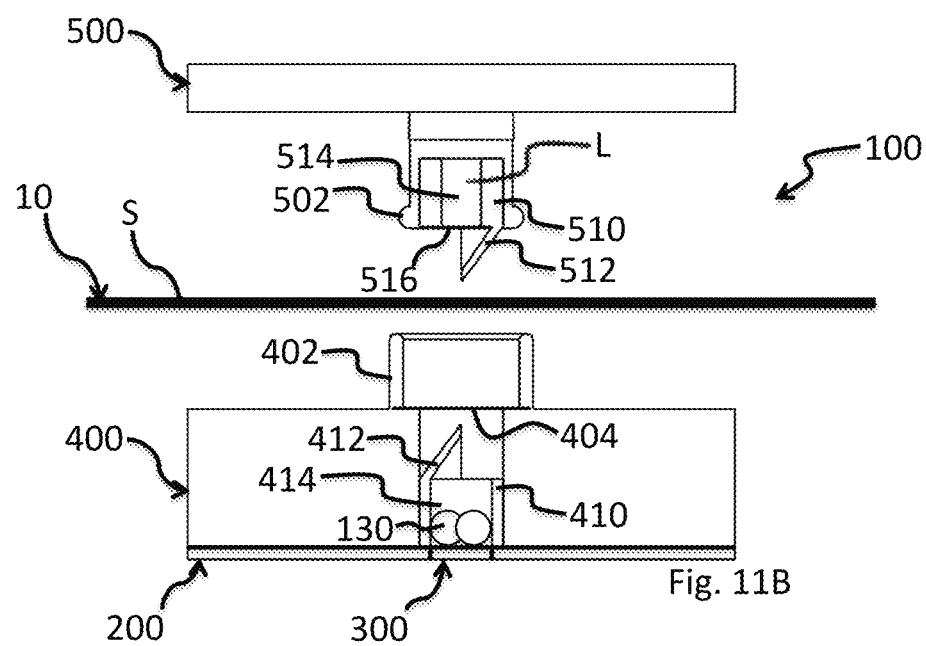

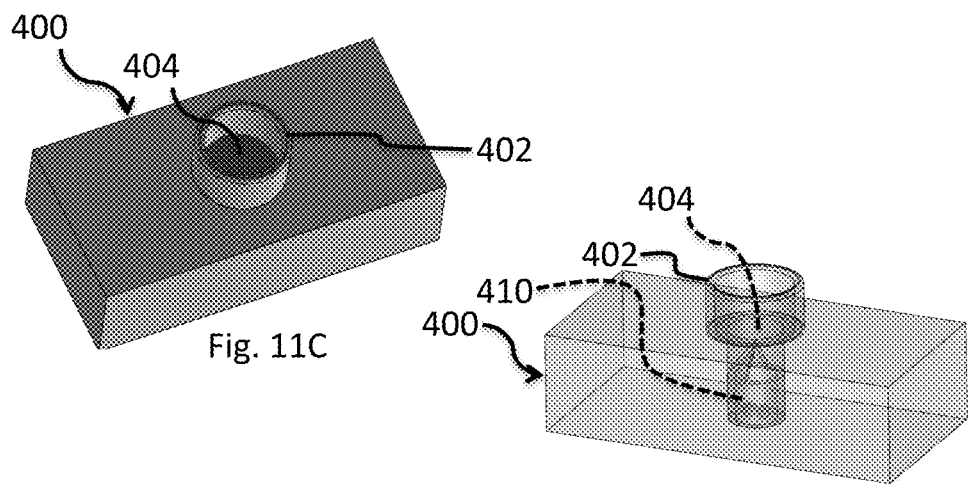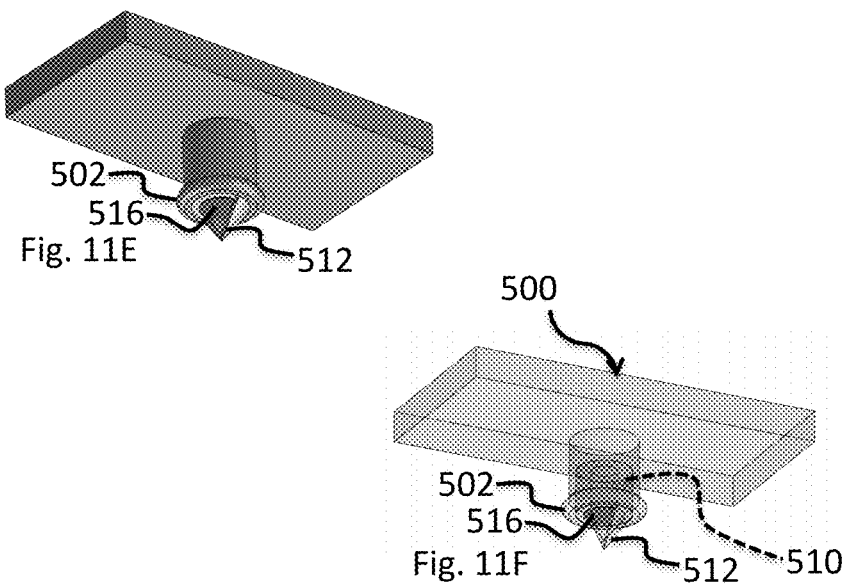

US 9,469,871 B2

METHODS AND APPARATUS FOR POINT-OF-CARE NUCLEIC ACID AMPLIFICATION AND DETECTION

REFERENCE TO RELATED APPLICATIONS

The present application is a continuation-in-part and claims priority and benefit of the filing date of U.S. patent application Ser. No. 13/447,218, filed Apr. 14, 2012, now U.S. Pat. No. 8,911,941, which claims priority and benefit of the filing date of U.S. provisional patent application Ser. No. 61/475,257, filed Apr. 14, 2011, both of which are incorporated herein by reference in their entireties. Furthermore, the present application claims priority and benefit of the filing dates of U.S. provisional patent applications Ser. No. 61/818,891, filed May 2, 2013, and Ser. No. 61/894,392, filed Oct. 22, 2013, both of which are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for nucleic acid amplification and detection. More particularly, the present invention relates to methods and apparatus for point-of-care nucleic acid amplification and detection.

BACKGROUND

Polymerase Chain Reaction (PCR) is considered the gold standard for nucleic acid amplification and detection because the specificity and sensitivity of PCR are considerably higher than that of analogous Enzyme-Linked Immuno-Sorbent Assay ("ELISA") tests. However, PCR systems typically are costly and require very clean samples. Point-Of-Care (POC) PCR systems generally are not fully disposable, are not appropriate for unskilled use, require substantial power and/or contain complicated processing and readout. Thus, PCR traditionally has been limited to high resource, centralized laboratory settings.

In view of the foregoing, it would be desirable to provide methods and apparatus for point-of-care nucleic acid amplification and detection that overcome the drawbacks of previously known methods and apparatus.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 3A and 3B are side and isometric views of alternative apparatus and methods for preparing and transferring sample from the sample collector of FIG. 1 to point-of-care nucleic acid amplification and detection apparatus;

FIGS. 4A-4D are side-sectional and isometric views of additional alternative apparatus and methods for preparing and transferring sample from the sample collector of FIG. 1 to point-of-care nucleic acid amplification and detection apparatus;

FIG. 7A is an isometric view of the point-of-care nucleic acid amplification and detection apparatus of FIGS. 2-6 in thermal communication with a heating element, while

FIGS. 8A-8E are isometric, top, bottom and side-sectional views of an alternative embodiment of the methods and apparatus for point-of-care nucleic acid amplification and detection of FIGS. 2-7;

FIGS. 10A-10G are isometric top, isometric bottom, isometric detail, translucent detail and side-sectional detail views of another alternative embodiment of methods and apparatus for point-of-care nucleic acid amplification and detection; and FIGS. 11A-11J are side, side-sectional, isometric, and translucent isometric views of yet another alternative embodiment of methods and apparatus for point-of-care nucleic acid amplification and detection.

DETAILED DESCRIPTION

Although this disclosure is detailed and exact to enable those skilled in the art to practice the disclosed technologies, the physical embodiments herein disclosed merely exemplify the various aspects of the invention, which may be embodied in other specific structures. While the preferred embodiments are described, the details may be changed without departing from the invention, which is defined by the claims.

The present invention relates to methods and apparatus for nucleic acid amplification and detection. More particularly, the present invention relates to methods and apparatus for point-of-care nucleic acid amplification and detection. The apparatus and methods optionally may be used in a multiplexed fashion to detect multiple target nucleic acid sequences of interest (e.g., to detect at least two target nucleic acid sequences of interest), and the apparatus optionally may be configured for disposal after one-time use.

The apparatus preferable utilizes an isothermal nucleic acid amplification technique, e.g., loop-mediated isothermal amplification ("LAMP)", to reduce the instrumentation requirements associated with nucleic acid amplification. Detection of target amplification may be achieved, for example, via detection of a color shift and/or fluorescence in one or more dyes, such as hydroxynaphthol blue, picogreen, and/or SYBR green, added to the amplification reaction, or via a change in turbidity. Such colorimetric, fluorescent and/or turbidity detection may be performed visually by an operator and/or may be achieved utilizing an imaging technique, such as spectrophotometric and/or fluorescence imaging, as described below.

Figure 1:
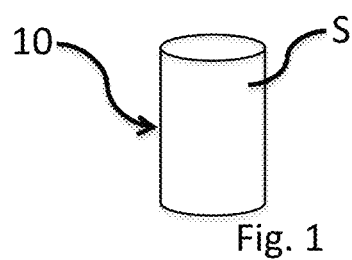
FIG. 1 is a schematic view of one embodiment of a sample collector.

FIG. 1 illustrates one embodiment of sample collector 10, per se known, for collecting a nucleic acid sample S. Sample collector 10 may, for example, comprise a sponge, foam or swab. Sample collector 10 may, for example, be fabricated from an inert polymer. Various sample matrices—including, but not limited to, food, urine, saliva, mucous, feces, blood, semen, tissue, cells, DNA, RNA, protein, plant matter, animal matter, liquids, solutions, solids, gases, and other sample matrices—may be deposited onto sample collector 10 as sample S.

In order to collect sample S with sample collector 10, the sample collector may, for example, be dipped or placed into one or more sample matrices of interest. In one method of using sample collector 10, the sample collector may be placed in a person's mouth for a period of time in order to collect a saliva sample S. Additionally or alternatively, one or more drops of one or more sample matrices of interest may, for example, be placed or deposited onto the sample collector. As yet another alternative, sample collector 10 may, for example, be swabbed or wiped across one or more sample matrices or surfaces of interest.

After collection of sample S, the sample may be transferred from sample collector 10 to point-of-care nucleic acid amplification and detection apparatus 100. Optionally, the sample may be prepared before, during or after transfer, e.g., via placement of sample S in fluid communication with lysis chemicals. Sample collector 10 optionally may comprise lysis chemicals that prepare sample S. Additionally or alternatively, sample S may be prepared via heat treatment. For example, sample S may be heated to a temperature higher than that required for isothermal amplification, e.g., higher than that required for loop-mediated isothermal amplification ("LAMP"). In some embodiments, sample S may comprise whole blood, which may, for example, be heat treated at about 99° C., e.g., for about 10 minutes, to achieve sample preparation. Other preparation methods, per se known, additionally or alternatively may be used. In some embodiments, sample S may not require preparation. In some embodiments, mixing of sample S with water, buffer and/ or dye solution may be sufficient to prepare the sample for nucleic acid amplification.

Figure 2A:
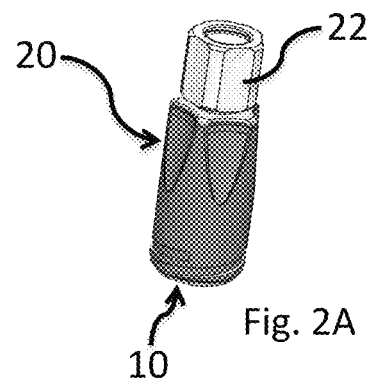
FIGS. 2A-2C are isometric and side views of apparatus and methods for preparing and transferring sample from the sample collector of FIG. 1 to point-of-care nucleic acid amplification and detection apparatus.
Figure 2B:
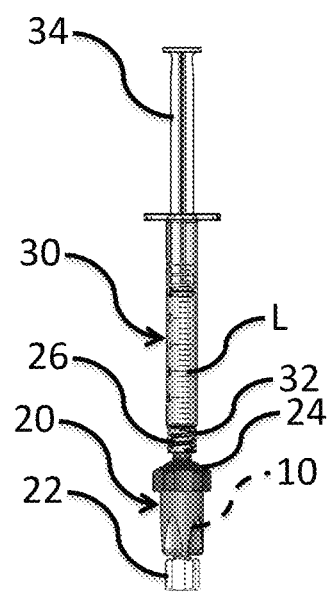

FIGS. 2 illustrate one embodiment of methods and apparatus for transferring sample S from sample collector 10 to point-of-care nucleic acid amplification and detection apparatus 100. As seen in FIG. 2A, sample collector 10 may be placed within sample collector containment element 20 having luer lock 22. Containment element 20 comprises a lumen or compartment in which sample collector 10 may be placed. As seen in FIG. 2B, cap 24 having luer lock 26 may be attached to sample collector containment element 20 after placement of sample collector 10 within the containment element 20. Containment element 20 and sample collector 10 then may be attached to syringe 30 via mating of (male or female) luer lock 26 of cap 24 with (female or male) luer lock 32 of syringe 30.

Figure 2C:
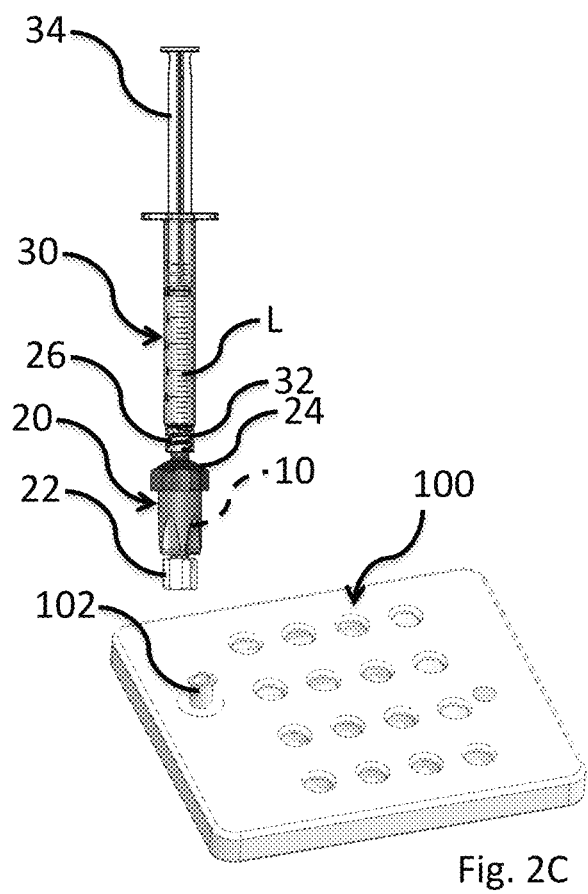

As seen in FIG. 2C, syringe 30 and containment element 20 with sample collector 10 may be coupled to point-of-care nucleic acid amplification and detection apparatus 100 by mating of (male or female) luer lock 22 of containment element 20 with (female or male) luer lock 102 of apparatus 100. Syringe 30 may contain liquid L (e.g., water, buffer and/or colorimetric or other dye solution) for eluting sample S from sample collector 10 into apparatus 100 via depression of plunger 34. Luer lock 102 of apparatus 100 (and/or the syringe or other alternative delivery device for delivering sample S) optionally may comprise a one-way valve that prevents backflow during nucleic acid amplification and detection.

FIGS. 3 illustrate alternative methods and apparatus for transferring sample S from sample collector 10 to apparatus 100. As seen in FIG. 3A, luer lock 22 of containment element 20 may be coupled to luer lock 42 of second syringe 40. Plunger 34 of syringe 30 may be depressed to elute liquid L and sample S from sample collector 10 into second syringe 40. Elution of liquid L and sample S into second syringe 40 before transfer of the sample to apparatus 100 may enhance mixing of the liquid and the sample before transfer to apparatus 100. Furthermore, sample S optionally may be collected and/or eluted multiple times into second syringe 40 before transfer to apparatus 100.

As seen in FIG. 3B, after collection of sample S and liquid L within second syringe 40, second syringe 40 may be detached from syringe 30, containment element 20 and sample collector 10. Second syringe 30 then may be coupled to apparatus 100 by mating of luer lock 42 to luer lock 102. Depression of plunger 44 forces sample S and liquid L into apparatus 100.

FIGS. 4 illustrate additional alternative methods and apparatus for transferring sample S from sample collector 10 to apparatus 100. As seen in FIG. 4A, sample collector 10 having sample S may be placed directly within syringe 30 by temporarily detaching plunger 34 from the syringe. Optionally, liquid L may be placed within syringe 30 along with sample collector 10 having sample S, though it should be understood that liquid L alternatively may be omitted. After placement of sample collector 10 within syringe 30, plunger 34 may be reattached to the syringe, as in FIG. 4B. Syringe 30 then may be coupled to apparatus 100 by mating of luer lock 32 with luer lock 102, as in FIG. 4C. Depression of plunger 34, as in FIG. 4D, compresses sample collector 10 and expresses sample S into apparatus 100.

Figure 5:
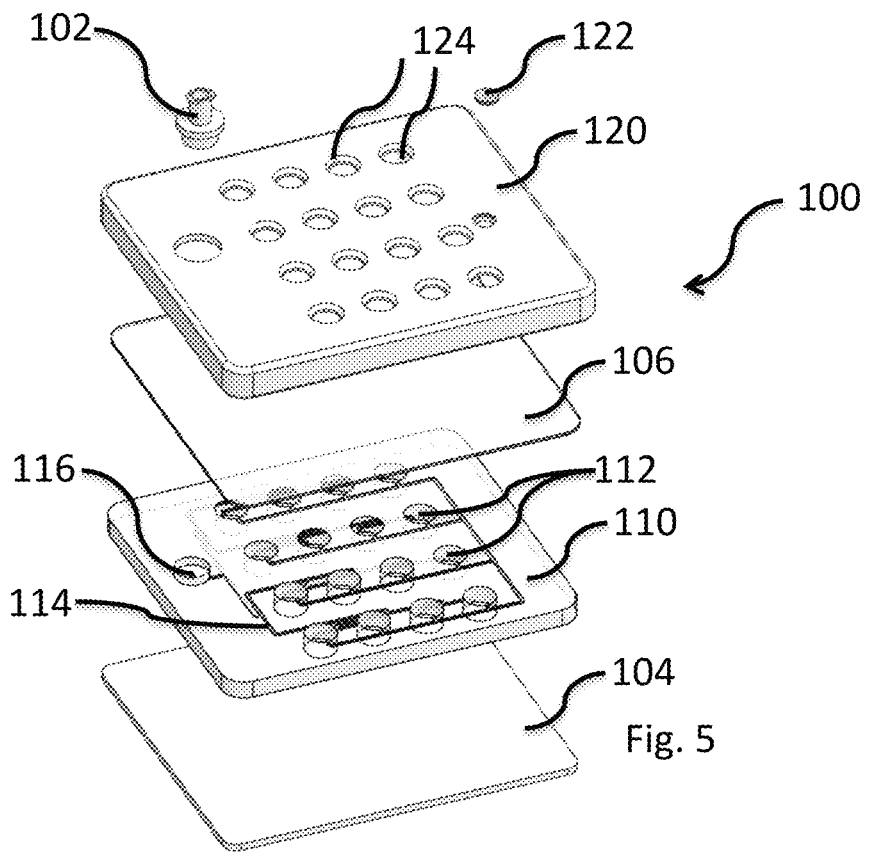
FIG. 5 is an exploded assembly view of the point-of-care nucleic acid amplification and detection apparatus of FIGS. 2-4.

With reference now to FIG. 5, a first embodiment of fully integrated sample-to-answer molecular diagnostic apparatus 100 for point-of-care nucleic acid amplification and detection is described. Apparatus 100 comprises luer lock 102 that is connected to channel and chamber element 110. Element 110 may, for example, be fabricated from polypropylene.

Channel cover 104 connects to the bottom of element 110, e.g., via adhesive or screws, while chamber cover 106 connects to the top of element 110, e.g., via adhesive or screws. Covers 104 and 106 may, for example, comprise an adhesive film or tape. Chamber cover 106 (and, optionally, channel cover 104) preferably is translucent or transparent to facilitate visual inspection of the contents of reaction chambers 112 of element 110. Apparatus 100 also may comprise top cover 120 with air filter 122, as well as chamber windows 124 that align with chambers 112 of element 110. In some embodiments, each chamber 112 may have a volume less than about 100 microliters, e.g., a volume on the order of about 30 microliters.

Figure 6:
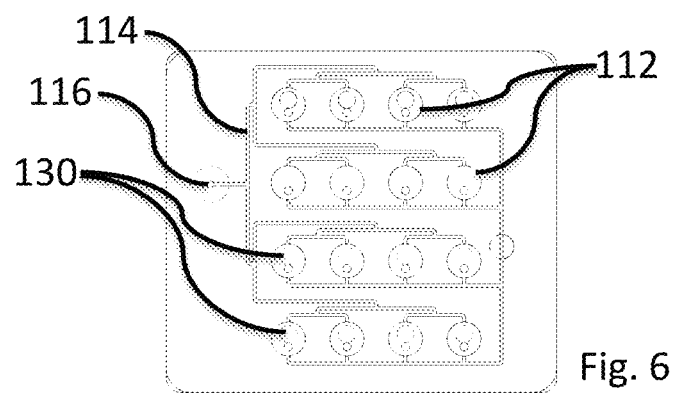
FIG. 6 is a bottom view of a channel and chamber element of the point-of-care nucleic acid amplification and detection apparatus of FIG. 2-5.

As seen in FIGS. 5 and 6, reaction chambers 112 of element 110 are connected to inlet 116 via (preferably equal length) microfluidic channels 114. Sample S is collected and expressed into apparatus 100 through luer lock 102, e.g., via depression of a syringe plunger as described previously with respect to FIGS. 2-4. Continued expression of samples S, e.g., via continued depression of the syringe plunger, forces sample S from inlet 116 through microfluidic channels 114 into chambers 112. Each chamber 112 contains reagents 130 for conducting nucleic acid amplification. Reagents 130 may, for example, comprise enzyme and master mix. When conducting nucleic acid amplification via LAMP, the enzyme may, for example, comprise Bst DNA polymerase, Bst 2.0 WarmStart DNA Polymerase, and/or Bsm DNA polymerase (and, optionally, a reverse transcriptase). The master mix may, for example, comprise primers, dNTPs, $MgSO_4$, betaine and/or excipients (e.g., mannitol, trehalose and/or dextrin). Reagents 130 also may comprise water, TE buffer, isothermal buffer and/or other buffers, which optionally may be delivered to chambers 112 via microfluidic channels 114, e.g., before, during and/or after delivery of sample S, e.g., as liquid L.

Reagents 130 also may comprise one or more dyes to facilitate detection of nucleic acid amplification, such as hydroxynaphthol ("HNB") blue. Detection of target amplification may be achieved, for example, via detection of a color shift in the colorimetric dye in the presence of amplicon, e.g., due to a shift in free magnesium ($Mg^{2+}$) concentration during LAMP amplification. Such colorimetric detection may be performed visually by an operator or may be achieved utilizing spectrophotometric imaging, as described below. In addition or as an alternative to colorimetric amplification detection with a colorimetric dye, a fluorescent dye, such as picogreen or SYBR green, may be utilized to detect amplification via fluorescence.

One or more of the reagents 130 preferably are lyophilized, e.g., to facilitate long-term storage. Additionally or alternatively, one or more of the reagents temporarily may be sequestered from one or more of the other reagents prior to nucleic acid amplification. Such temporary reagent sequestration may facilitate long-term storage of the reagents and/or may forestall reagent mixing (and, thereby, nucleic acid amplification) until desired, e.g., until the reagents have been exposed to sample S. For example, the enzyme may be sequestered from the master mix.

In some embodiments, one or more of the reagents 130 may be temporarily sequestered within one or more temporary sequestration vessels. In some embodiments, the temporary sequestration vessel(s) may, for example, comprise one or more thermal encasement materials that are configured to melt, become porous or otherwise release the sequestered reagent(s) 130 upon heating, e.g., during nucleic acid amplification. The thermal encasement material(s) may, for example, comprise polycaprolactone, and/or phase change materials such as paraffin or wax. In some embodiments, the temporary sequestration vessel(s) may comprise one or more blister packs or other containers such as gel caps that may be punctured or otherwise opened to release the sequestered reagent(s) 130. When the temporary sequestration vessel(s) comprise gel caps, they optionally may be opened via hydrolysis in addition or as an alternative to puncturing.

Upon delivery of sample S to chambers 112 through microfluidic channels 114, each reagent-containing chamber 112 is configured to amplify a nucleic acid target sequence of interest, if contained in the sample S. Different chambers 112 optionally may utilize different primers to facilitate amplification and detection of different target sequences of interest (i.e., to facilitate multiplexed nucleic acid amplification and detection) in different chambers. A fraction of the chambers 112 may serve as positive controls (e.g., may be preloaded with one or more target nucleic acid sequences of interest that are expected to amplify during nucleic acid amplification). Additionally or alternatively, a fraction of the chambers 112 may serve as negative controls (e.g., may comprise reagents 130 but may not be connected to microfluidic channels 114 such that they do not contain sample S).

Figure 7A:
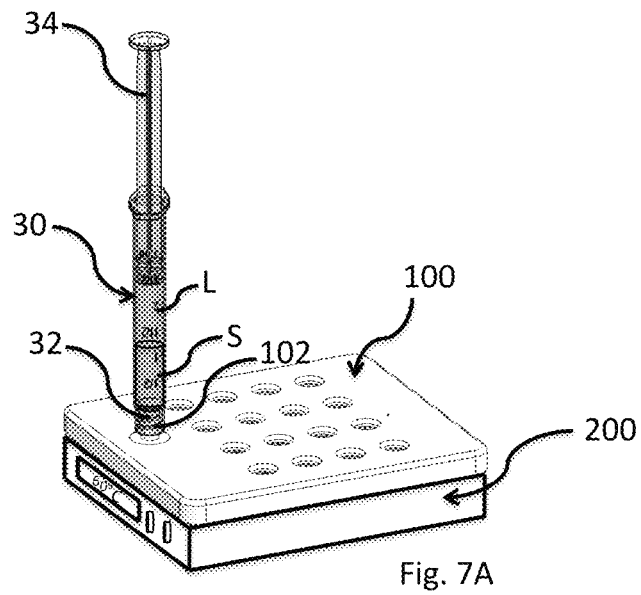

After delivery of sample S to chambers 112, the chambers may be heated, e.g., isothermally heated, to amplify the one or more target nucleic acid sequences of interest. When conducting isothermal nucleic acid amplification via LAMP, the contents of chambers 112 may be heated in the range of about 60° C.-65° C. for about 5-70 minutes. As seen in FIG. 7A, the contents of chambers 112 may be heated via a heating element 200 that is thermally coupled to apparatus 100. Such heating may be achieved utilizing any of variety of techniques, including (but not limited to) electrical, chemical and/or electrochemical techniques. Heating element 200 may, for example, comprise a resistive heater connected to a power supply, such as one or more batteries or a wall outlet connection, and an optional temperature controller for resistively heating the contents of chambers 112. Additionally or alternatively, heating element 200 may comprise a diamond/tungsten heater, an inductive heater, a chemical heater (e.g., an exothermic chemical heater, such as a supersaturated sodium acetate heater, a cellulose/iron/water/activated carbon/vermiculite/salt heater, an iron oxide heater, an iron/magnesium salt heater, a catalytic burner, a fuel cell heater, etc.). Heating element 200 may be reusable or may be configured for disposal after one-time use. Optionally, heating element 200 may be integrally connected to apparatus 100. Heating element 200 may be fully automated or may comprise controls that, e.g, allow the user to set a target temperature and duration of heating. Optionally, heating element 200 may comprise a phase change material, such as paraffin, for maintaining a desired temperature for an extended period of time.

Figure 7B:
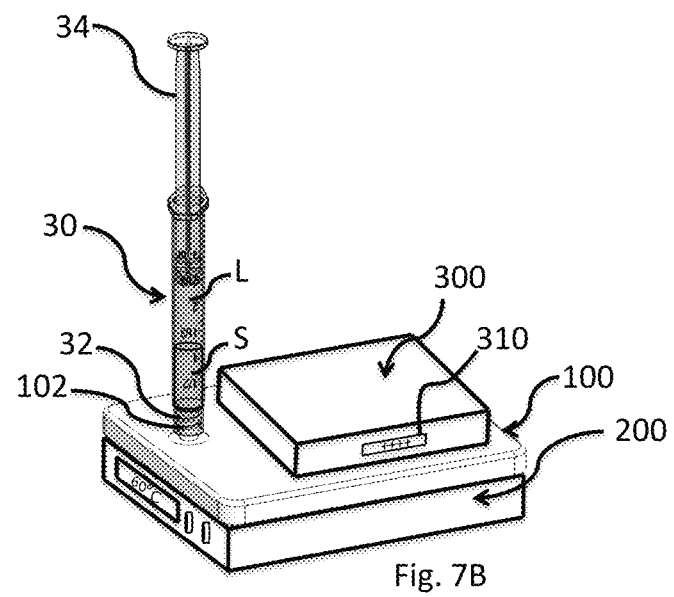
FIG. 7B is an isometric view of an optional detection sensor for use with the apparatus and method of FIG. 7A.

As discussed previously, detection of target amplification optionally may be achieved via detection of a color shift (i.e. a wavelength shift) and/or fluorescence (i.e., an intensity shift) in one or more dyes in the presence of amplicon. Such colorimetric and/or fluorescence detection may be performed visually by an operator and/or may be achieved utilizing an imaging technique, such as spectrophotometric and/or fluorescence imaging. In the embodiment of FIG. 7B, sensor 300, such as spectrophotometric CMOS or CCD imaging sensor 300, is in proximity to chambers 112 for detection of a color shift, fluorescence, turbidity or some other change indicative of target nucleic acid sequence amplification. Chamber cover 106 (see FIG. 5) preferably is transparent to facilitate detection of changes within the reaction chambers. In some embodiments, sensor 300 may be integrally connected to element 110 and may cover chambers 112, obviating chamber cover 106.

Sensor 300 optionally may comprise a coating, such as an Indium Tin Oxide ("ITO") coating, which may be utilized in addition or as an alternative to heating element 200 to resistively heat the contents of each chamber 112 to achieve target nucleic acid amplification. The coating may be placed in proximity to chambers 112. As discussed previously, when conducting isothermal amplification via LAMP, the contents of chambers 112 may be heated in the range of about 60° C.-65° C. for about 5-70 minutes.

Imaging sensor 300 may measure a baseline color of reagents 130 and sample S prior to isothermal heating, and a final color of the reagents after isothermal heating (e.g., after isothermal heating). Since the reagents 130 within each reaction chamber 112 may, for example, include a colorimetric (or fluorescent) dye that shifts in color, e.g., from purple to blue, upon amplification of a target nucleic acid sequence, any such shift in color within the chambers may be detected by the imaging sensor 300 as a differential between the baseline and final color, and this differential may be indicative of target amplification. As seen in FIG. 7B, optional digital readout or display 310 may output detection results (and/or instructions) to the user, removing any risk of detection ambiguity. While the embodiment of FIG. 7B illustratively achieves colorimetric or fluorescence detection via spectrophotometric imaging, it should be understood that such colorimetric or fluorescence detection additionally or alternatively may be performed visually by an operator.

Heating element 200 and/or sensor 300 may comprise a logic chip for controlling operation of the heating element and/or the sensor, for controlling nucleic acid amplification via heating of chambers 112, for comparing baseline and final color measurements taken with sensor 300 to determine whether amplification has occurred, and/or for controlling the display of instructions or detection results via display 310. Wires and/or a circuit board may connect the logic chip to heating element 200, sensor 300 and/or a power supply. The power supply may, for example, comprise one or more batteries or a wall outlet connection.

With reference now to FIG. 8, an alternative embodiment of apparatus 100 is described. In the embodiment of FIG. 8, element 110' comprises four chambers 112 rather than sixteen (as will be apparent to those of skill in the art, any number of chambers 112 may be provided). Element 110' comprises vent channels 118 in fluid communication with the top of each chamber 112 for venting air from the chambers to the atmosphere. Microfluidic channels 114 deliver sample S to the bottom of each chamber 112, and vent channels 118 vent overflow from the top of each chamber out of apparatus 100 through breathable membrane or one-way valve 119. FIG. 8A is an isometric view of apparatus 100. In the top view of element 110' seen in FIG. 8B, the fluid communication of vent channels 118 with the tops of chambers 112 is visible. In the bottom view of element 110' seen in FIG. 8C, the extension of microfluidic channels 114 from inlet 116 to chambers 112 is visible, as is membrane or valve 119. The side-sectional view of FIG. 8D is taken through luer lock 102 and the outlet of vent channels 118. The side-sectional view of FIG. 8E is taken through a chamber 112 and shows the fluid communication of microfluidic channels 114 with the bottom of the chamber and of vent channels 118 with the top of the chamber.

FIGS. 9 provide another alternative embodiment of apparatus 100 comprising element 110". FIG. 9A provides an isometric view of apparatus 100, FIG. 9B shows a top view of element 110" of the apparatus with chamber cover 106 removed, and FIG. 9C shows a bottom view of the element 110" with channel cover 104' removed. While the embodiment of apparatus 100 shown in FIGS. 8 comprises venting of air from chambers 112 to the atmosphere via vent channels 118 and membrane or valve 119 of element 110', the embodiment of apparatus 100 shown in FIGS. 9 vents air from chambers 112 through vent channels 118' to one or more overflow chamber(s) 125 of element 110" (see FIG. 9C), rather than venting to the atmosphere. Thus, apparatus 100 of FIGS. 9 is fully contained. Overflow chamber(s) 125 preferably are sized to limit a pressure increase in the overflow chamber(s) during nucleic acid amplification to less than about 5-10 psi.

Figure 9A:
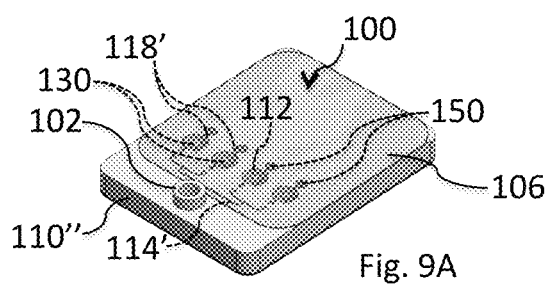
FIGS. 9A-9J are isometric, top, bottom, assembly, side-sectional detail, and translucent isometric views of another alternative embodiment of methods and apparatus for point-of-care nucleic acid amplification and detection.
Figure 9B:
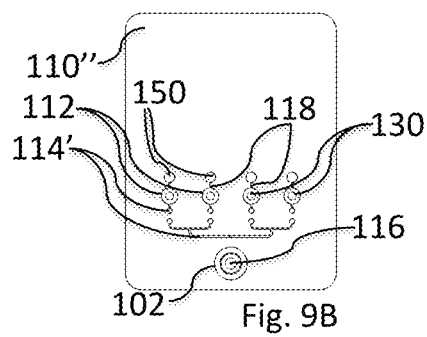
Figure 9C:
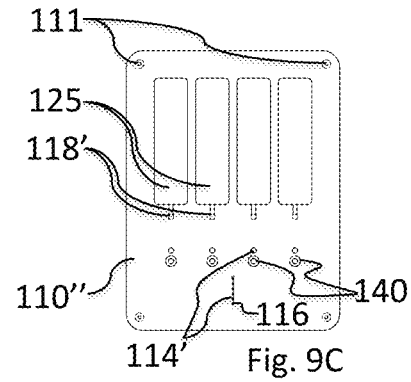
Figure 9D:
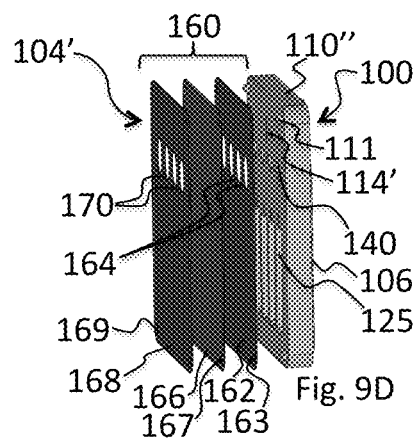
Figure 9E:
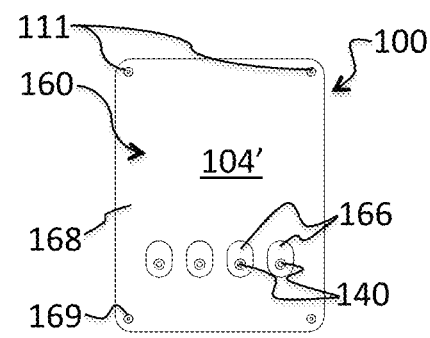

As best seen in FIG. 9C, element 110" also comprises anti-backflow valves 140 that prevent cross-contamination between chambers 112 via backflow across microfluidic channels 114'. Furthermore, as best seen in FIG. 9B, element 110" comprises flow control media 150 positioned along vent channels 118 between chambers 112 and overflow chamber(s) 125 that allow venting of air or other gases from the chambers 112 but not fluid, thereby ensuring equal fill of sample S in all chambers 112 while releasing excess pressure.

Element 110" of FIGS. 9 has shorter microfluidic channels 114' as compared to microfluidic channels 114 of element 110' of FIGS. 8. Shorter microfluidic channels reduce the priming volume over which sample S must travel to reach chambers 112. Element 110" may have a priming volume on the order of 20-50 microliters. In contrast to previously described microfluidic channels 114, microfluidic channels 114' extend along both the top and the bottom of element 110", as well as through the element 110". The circuitous path of microfluidic channels 114' is described in more detail below.

In the embodiment of FIGS. 9, channel cover 104' comprises laminate 160 that, in addition to covering the portion of microfluidic channels 114' positioned on the bottom of element 110", works in conjunction with anti-backflow valves 140 to prevent cross-contamination between chambers 112. In one embodiment seen in the exploded assembly view of FIG. 9D, laminate 160 comprises double-sided adhesive layer 162, elastomer layer 166 and optional single-sided adhesive backing layer 168. Element 110" comprises optional registration posts 111 for aligning the layers of laminate 160 during attachment of the laminate to element 110". Layer 162 comprises optional registration cutouts 163 that align with registration posts 111. Similarly, layer 166 comprises optional registration cutouts 167, while layer 168 comprises optional registration cutouts 169. Layer 162 also comprises valve cutouts 164 that encircle anti-backflow valves 140, while layer 168 comprises valve cutouts 170. Double-sided adhesive layer 162 is attached to element 110" and to elastomer layer 166. Optionally, single-sided adhesive backing layer 168 may be connected to elastomer layer 166 to reduce a risk of laminate 160 delaminating. FIG. 9E is a bottom view of apparatus 100 with channel cover 104' attached.

Figure 9F:
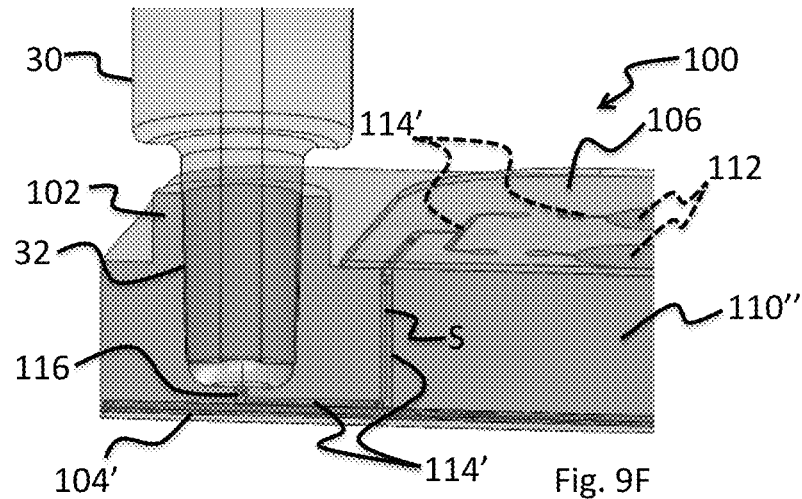
Figure 9G:
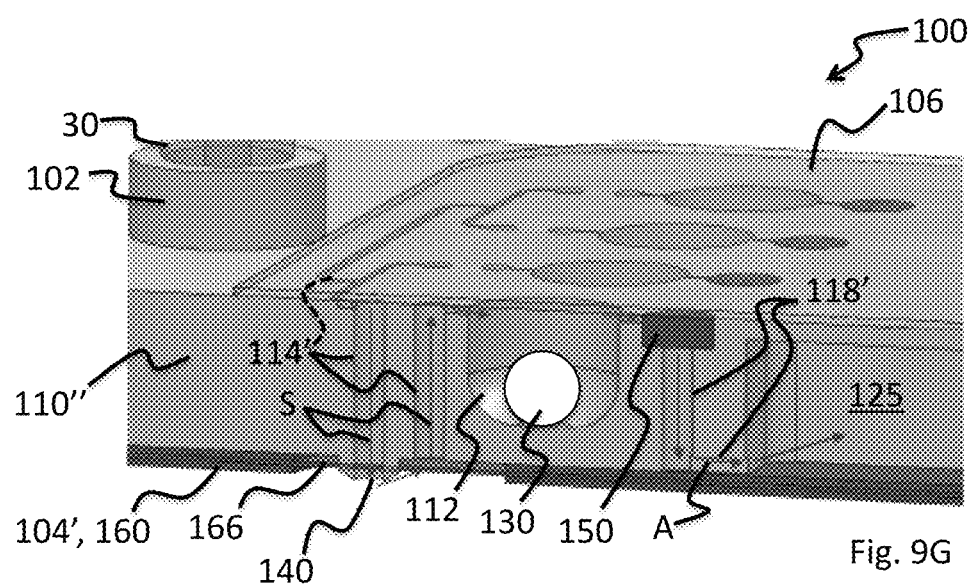

With reference now to FIGS. 9F and 9G in conjunction with FIGS. 9A-9E, a method of using the embodiment of apparatus 100 shown in FIGS. 9 is described. As seen in FIG. 9F, syringe 30 (or any other sample transfer device, e.g., previously described syringe 40 or previously described syringe 30 with containment element 20) is coupled to apparatus 100 via mating of luer lock 32 with luer lock 102. Syringe 30 expresses sample S (and, optionally, liquid L) into apparatus 100 through inlet 116. Sample S travels along the bottom of element 110" within microfluidic channel 114' (see FIG. 9F in conjunction with FIG. 9C). The microfluidic channel then passes through element 110" and takes sample S to the top of the element 110" before branching into multiple microfluidic channels 114' (see FIG. 9F in conjunction with FIG. 9B). The microfluidic channels 114' then travel back through element 110" and deliver sample S to anti-backflow valves 140. Pressure applied via syringe 30 causes elastomer layer 166 of laminate 160 to locally and temporarily deflect in the immediate vicinity of valves 140, thereby allowing passage of sample S (see FIG. 9G in conjunction with FIG. 9C). After passage of sample S, anti-backflow valves 140 reseal to prevent backflow of sample S and, thereby, cross-contamination of chambers 112. As best seen in FIG. 9G in conjunction with FIG. 9C, microfluidic channels 114' take sample S that has passed through valves 140 back to the top of element 110" and into chambers 112. Chambers 112 comprise reagents 130, e.g., lyophilized reagents 130.

Vent channels 118' extend from chambers 112 for venting of air A from chambers 112 to overflow chamber(s) 125 (see FIG. 9G in conjunction with FIGS. 9B and 9C). Flow control media 150 are positioned within channels 118' between chambers 112 and overflow chamber(s) 125. Flow control media 150 may, for example, comprise a small pore hydrophobic material that allows passage of air but not fluid. After air passes through flow control media 150, it travels within vent channels 118' from the top of element 110'' through the element to overflow chamber(s) 125.

As with all other embodiments of apparatus 100, the embodiment of apparatus 100 shown in FIGS. 9 may comprise or be coupled to a heating element (e.g., heating element 200 of FIGS. 7) for amplifying one or more target nucleic acid sequence(s) of interest, when present in sample S, via reagents 130. Target sequence amplification may be detected visually by an operator, e.g. by visual detection of a visual indicator such as a color shift in a colorimetric dye or a turbidity change, or automatically, e.g. via a sensor (such as sensor 300 of FIG. 7B) that detects amplification by detection of a visual indicator (color shift, fluorescence, turbidity change, etc.). The embodiment of apparatus 100 shown in FIGS. 9 illustratively comprises both air overflow chambers 125 and anti-backflow valves 140. It should be understood that apparatus alternatively may comprise only the anti-backflow valves or only the overflow chambers.

Figure 9H:
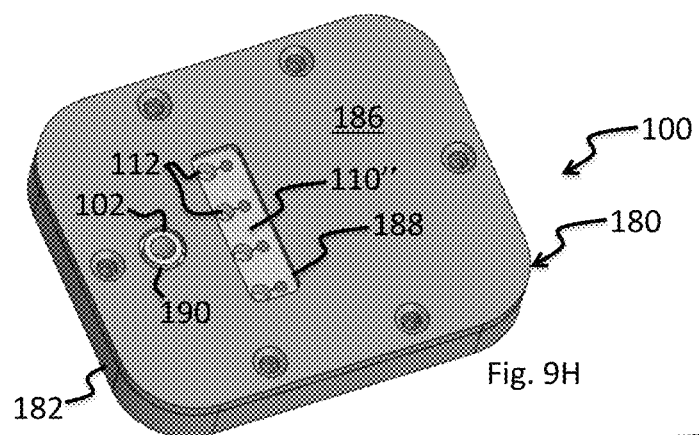
Figure 9I:
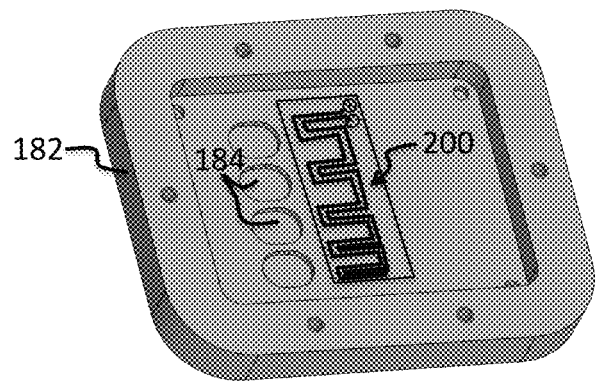
Figure 9J:
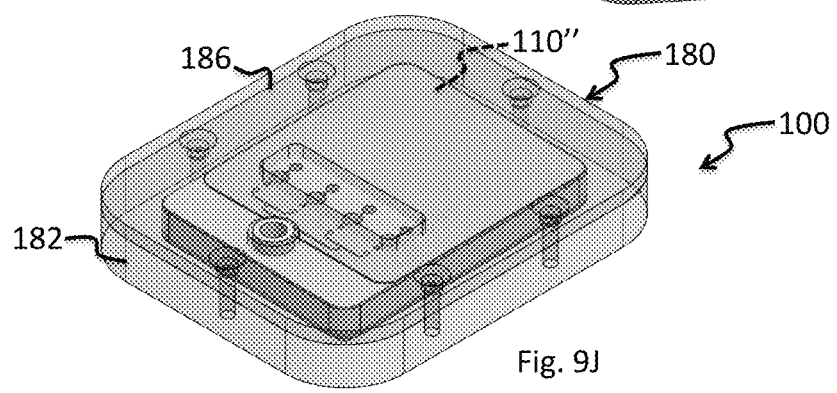

Referring now to FIGS. 9H-9J, apparatus 100 optionally may comprise case 180 that contains apparatus 100. Case 180 may comprise cavity 182 with indentations 184 configured to receive anti-backflow valves 140 of element 110''. Heating element 200 also may be positioned within cavity 182 in the vicinity of chambers 112 for heating the contents of chambers 112. Case 180 further comprises cover 186 with chamber cutout 188 to facilitate visualization of chambers 112, and with luer lock cutout 190 to provide access to luer lock 102. Cover 186 firmly attaches to cavity 182, e.g., via screws or a press fit, to form case 180 with the other components of apparatus 100 disposed therein.

FIGS. 10 provide another alternative embodiment of apparatus 100 comprising element 110'''. The embodiment of apparatus 100 shown in FIGS. 10 comprises anti-backflow locking valve 200 that is configured to lock microfluidic channels 114'' of element 110''' in either an open position that allows flow through the channels 114'' or a closed position that prevents backflow and cross-contamination between chambers 112 via channels 114''. Such locking of the channels may be made reversible or irreversible, as desired. FIG. 10A provides an isometric top view of apparatus 100, while FIG. 10B provides an isometric bottom view of the apparatus. FIG. 10C provides an isometric detail view of anti-backflow locking valve 200. For the sake of clarity, chamber cover 106 and channel cover 104 are not shown in FIGS. 10. However, it should be understood that they may be provided as described with respect to prior embodiments of the apparatus.

As seen in FIGS. 10A and 10B, anti-backflow locking valve 200 is configured for placement inside void 202 of element 110''' in order to lock channels 114'' in the open (i.e. flow-enabled) or closed (i.e., flow-blocked) position, as desired, by sliding the locking valve 200 within void 202 relative to the element 110'''. As seen in FIG. 10C, lumens 230 pass through anti-backflow locking valve 200 and may be selectively aligned and unaligned with channels 114'' to unlock and lock the channels, respectively. Locking valve 200 may, for example, comprise relatively stiff or rigid substrate 210 with elastomeric overmold 220. Elastomeric overmold 220 may comprise O-ring elements 222a and 222b that are configured to create a fluid-tight seal against element 110'''. O-ring elements 222a are associated with the locked configuration of anti-backflow lock 200 that prevents cross-contamination between chambers 112 by blocking channels 114''. O-ring elements 222b are concentrically aligned with lumens 230 and are associated with the unlocked configuration of anti-backflow locking valve 200 that allows fluid flow through channels 114''. In an alternative embodiment of locking valve 200 (not shown), elastomeric overmold 220 may be omitted, and O-ring elements 222a and/or 222b may be formed or attached directly to substrate 210. Locking valve 200 preferably comprises enlarged end 240 that facilitates manipulation of the locking valve during use (i.e., that may be grasped by the user for sliding the locking valve from the unlocked to the locked configuration, or vice versa).

Figure 10D:
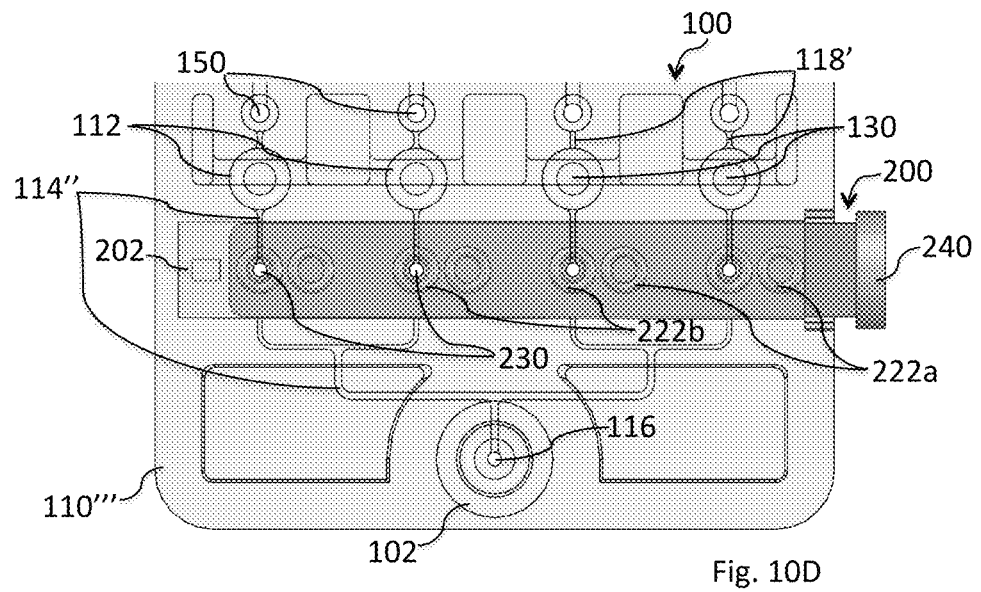
Figure 10E:
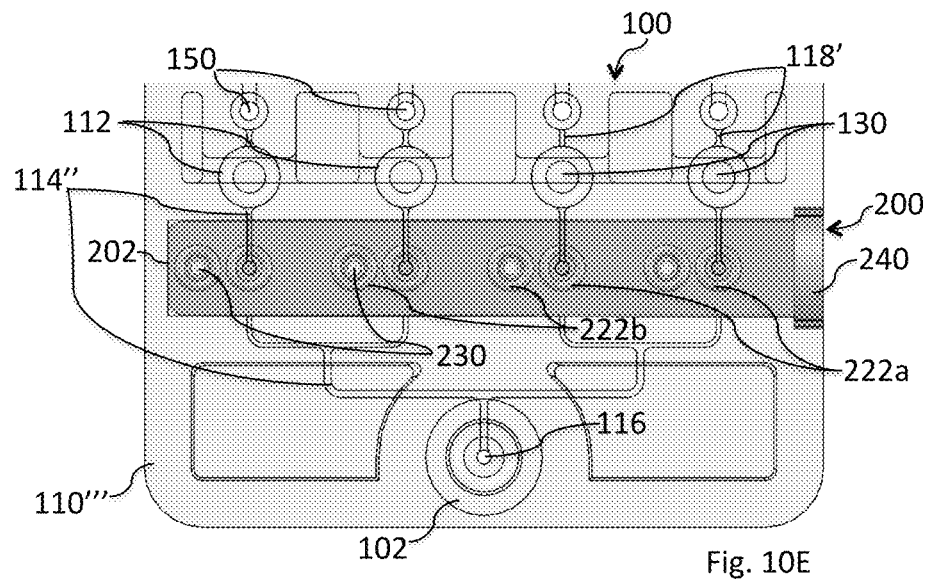

FIGS. 10D and 10E are translucent detail views that illustrate actuation of locking valve 200. As seen in FIG. 10D, channels 114'' may be placed in the unlocked configuration by positioning locking valve 200 within void 202 of element 110''' such that lumens 230 are aligned with microfluidic channels 114''. Optionally, locking valve 200 and/or void 202 may be lubricated to facilitate sliding of the lock relative to the void. In this unlocked configuration, O-ring elements 222b create fluid seals around the perimeters of channels 114'' such that sample may flow from a sample transfer device (e.g., a syringe) through the first section of channels 114'', through lumens 230 and through the second section of the channels 114'' to chambers 112. As seen in FIG. 10E, locking valve 200 then may be slid within void 202 to place channels 114'' in the locked configuration such that lumens 230 are out of alignment with the microfluidic channels. In this locked configuration, O-ring elements 222a create fluid seals around the perimeters of channels 114'', thereby isolating and blocking each channel 114'' from the others and preventing cross-contamination between chambers 112 via backflow through the channels.

In one embodiment, enlarged end 240 of locking valve 200 may sit flush with element 110''' in the locked configuration of FIG. 10E, such that the user is unable to grasp end 240 and unlock channels 114'' once locking valve 200 has blocked the channels. Such an irreversible locking valve may reduce a risk of backflow contamination or of accidental venting of sample to the environment. In an alternative embodiment, enlarged end 240 of locking valve 200 may protrude from element 110''' in the locked configuration, such that the user may grasp end 240 for reversible locking and unlocking of channels 114'' with locking valve 200.

Figure 10F:
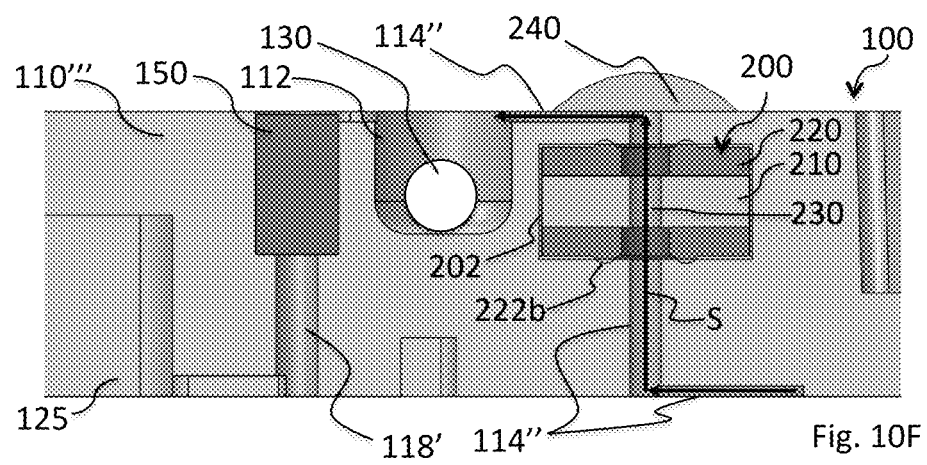
Figure 10G:
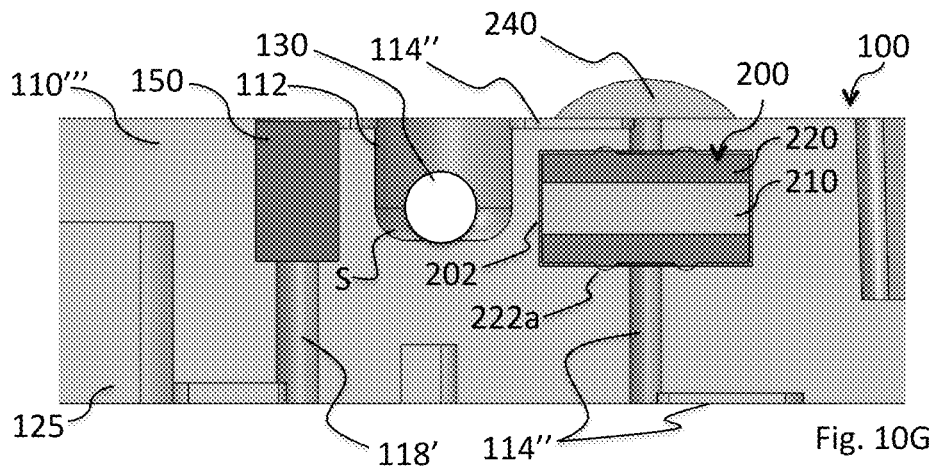

With reference now to FIGS. 10F and 10G in conjunction with FIGS. 10A-10E, a method of using the embodiment of apparatus 100 shown in FIGS. 10 is described. In FIG. 10F, locking valve 200 positions channels 114'' in the unlocked configuration shown in FIG. 10D. A syringe or other sample transfer device is coupled to apparatus 100 via mating with luer lock 102. The syringe or other sample transfer device expresses sample S (and, optionally, liquid L) into apparatus 100 through inlet 116. Sample S travels along the bottom of element 110''' within microfluidic channel 114'', which branches into multiple microfluidic channels 114'' (see FIG. 10F in conjunction with FIGS. 10B and 10D). Each microfluidic channel then passes through element 110''' via a lumen 230 of locking valve 200, thereby taking sample S to the top of the element 110''' and into chambers 112 having reagents 130 (e.g., lyophilized reagents 130). As seen in FIG. 10G, locking valve 200 then may be slid within void 202 relative to element 110'' in order to position channels 114'' in the locked configuration of FIG. 10E wherein the channels are blocked. Sample S cannot flow back through locking valve 200 when channels 114'' are in the locked configuration, which prevents cross-contamination of chambers 112 via backflow through the channels.

Element 110''' comprises previously described vent channels 118' that extend from chambers 112 for venting of air A (but not sample S) from the chambers 112 to overflow chamber(s) 125 (see FIG. 10G in conjunction with FIGS. 10A and 10B). Flow control media 150 are positioned within channels 118' between chambers 112 and overflow chamber(s) 125. Flow control media 150 may, for example, comprise a small pore hydrophobic material that allows passage of air but not fluid. After air passes through flow control media 150, it travels within vent channels 118' from the top of element 110''' through the element 110''' to overflow chamber(s) 125. The embodiment of apparatus 100 shown in FIGS. 10 illustratively comprises both air overflow chambers 125 and anti-backflow locking valve 200. It should be understood that the apparatus alternatively may comprise only the anti-backflow lock or only the overflow chambers.

As with all other embodiments of apparatus 100, the embodiment of apparatus 100 shown in FIGS. 10 may comprise or be coupled to a heating element (e.g., heating element 200 of FIGS. 7) for amplifying one or more target nucleic acid sequence(s) of interest, when present in sample S, via reagents 130. Target sequence amplification may be detected visually by an operator, e.g. by visual detection of a visual indicator such as a color shift in a colorimetric dye or a turbidity change, or automatically, e.g. via a sensor (such as sensor 300 of FIG. 7B) that detects amplification by detection of a visual indicator (color shift, fluorescence, turbidity change, etc.). Optionally, the heating element, element 110''' and/or some other aspect of apparatus 100 may comprise a geometric or other constraint that precludes coupling of element 110''' to the heating element when locking valve 200 is positioned in the open configuration allowing flow through channels 114". Such a constraint may reduce a risk of sample amplification before locking of channels 114" in the closed configuration, thereby reducing a risk of backflow-induced cross-contamination of chambers 112.

Embodiments of apparatus 100 described thus far have delivered sample S to reaction chambers 112 via microfluidic channels that distribute the sample S across the chambers. In the embodiment of apparatus 100 shown in FIGS. 11, sample S is delivered to a reaction chamber without microfluidics. The embodiment of apparatus 100 shown in FIGS. 11 illustratively comprises a single reaction chamber, but it should be understood that apparatus 100 may comprise any desired number of reaction chambers.

With reference to FIG. 11A, apparatus 100 comprises reaction chamber 400 and punch element 500. Punch element 500 comprises male element 502, which is configured to press fit into female element 402 of reaction chamber 400 and seal the reaction chamber 400 in advance of nucleic acid amplification and detection.

As seen in FIGS. 11B and 11D, female element 402 of reaction chamber 400 comprises reagent insert 410 that may be press fit therein. Reagent insert 410 comprises cutting element 412 and reagent chamber 414. Reagents 130 are positioned within reagent chamber 414. The reagents 130 may, for example, be in solution or liquid form. Alternatively, the reagents 130 may be lyophilized, as in FIGS. 10.

Reagent insert 410 is sealed within female element 402 of reaction chamber 400 via seal 404 (see, e.g., FIG. 11C). Seal 404 may, for example, comprise a metal foil or plastic film. Sealing of reaction chamber 400 may facilitate long-term storage of reagents 130 prior to use and/or may ensure that lyophilized reagents 130 remain dry prior to use.

As seen in FIGS. 11B, 11E and 11F, male element 502 of punch element 500 comprises liquid insert 510 that may be press fit therein. Liquid insert 510 comprises cutting element 512 and liquid chamber 514. Liquid chamber 514 is sealed with seal 516. Seal 516 may, for example, comprise a metal foil or plastic film. Liquid L, such as water and/or TE buffer, is sealed within liquid chamber 514. Dye, MgSO4, betaine and/or isothermal buffer additionally or alternatively may be sealed within chamber 514.

Apparatus 100 further comprises heating element 200, which is in thermal communication with the reaction chamber 400. Heating element 200, which optionally may be disposed of after single use along with the rest of apparatus 100, is configured to heat the contents of reaction chamber 400 to achieve nucleic acid amplification, e.g., isothermal nucleic acid amplification such as LAMP. Heating element 200 may comprise, for example, a resistive heater comprising an etched foil element encapsulated between two layers of polyimide film. The heating element further may comprise a power supply, such as batteries or connection to a standard wall outlet, as well as a thermocouple for temperature monitoring in a feedback loop with a temperature controller for adjusting the monitored temperature as desired to achieve nucleic acid amplification.

Reaction chamber 400 preferably is transparent or translucent to facilitate visualization of the reaction chamber in order to detect amplification of a target nucleic acid sequence of interest. Nucleic acid amplification may be detected via a color shift in a colorimetric dye, via an increase in turbidity, via fluorescence, etc. Detection may be achieved with the naked eye and/or via optional sensor 300, which may be disposable. Detection results may be shown on a display, which may be disposable.

Sample S may be placed directly into reaction chamber 400 and/or punch element 500 prior to sealing of the reaction chamber with the punch element. Alternatively, sample collector 10 comprising sample S may be positioned between the reaction chamber 400 and the punch element 500 such that mating of male element 502 with female element 402 places sample S within the reaction chamber 400, as shown in FIGS. 11. In the embodiment of FIGS. 11, sample collector 10 may, for example, comprise a filter paper, such as a chemically treated filter paper, e.g., Flinders Technology Associates ("FTA") cards available from Whatman (part of GE Healthcare). Various sample matrices—including, but not limited to, food, urine, saliva, mucous, feces, blood, semen, tissue, cells, DNA, RNA, protein, plant matter, animal matter, solutions, solids, and other sample matrices—may be deposited onto sample collector 10 (additional sample matrices will be apparent). In this manner, sample collector 10 may collect sample S via the filter paper.

In order to collect sample S with sample collector 10, the filter paper may, for example, be dipped or placed into one or more sample matrices of interest. Additionally or alternatively, one or more drops of one or more sample matrices of interest may, for example, be placed or deposited onto the filter paper. Additionally or alternatively, the filter paper may, for example, be swabbed or wiped across one or more sample matrices or surfaces of interest.

Figure 11G:
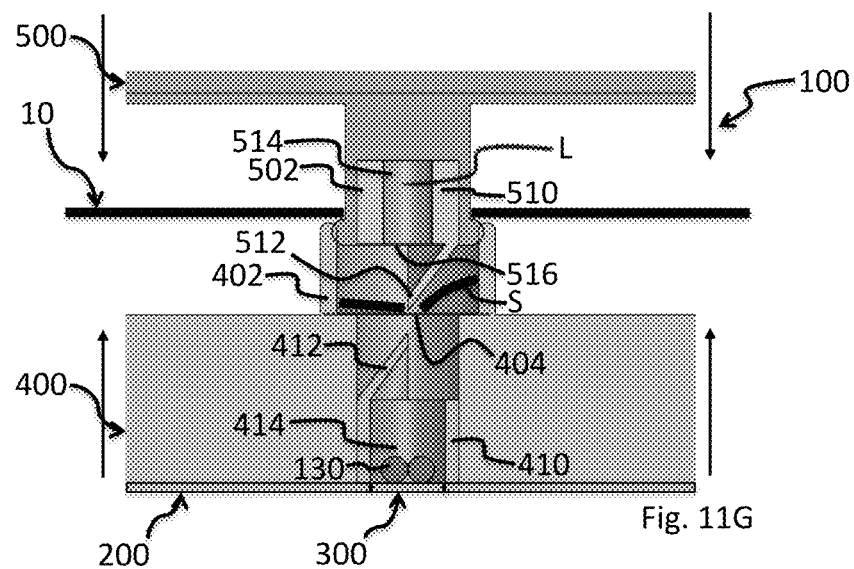

Referring now to FIGS. 11G-11J, a method of using the embodiment of apparatus 100 seen in FIGS. 11 is described. As seen in FIG. 11G, reaction chamber 400 and punch element 500 are approximated, such that male element 502 of the punch element mates with female element 402 of the reaction chamber to seal the reaction chamber. Cutting element 512 of liquid insert 510 pierces sample collector 10, and male element 502 removes a punch of sample S from sample collector 10, thereby placing sample S within reaction chamber 400.

Figure 11H:
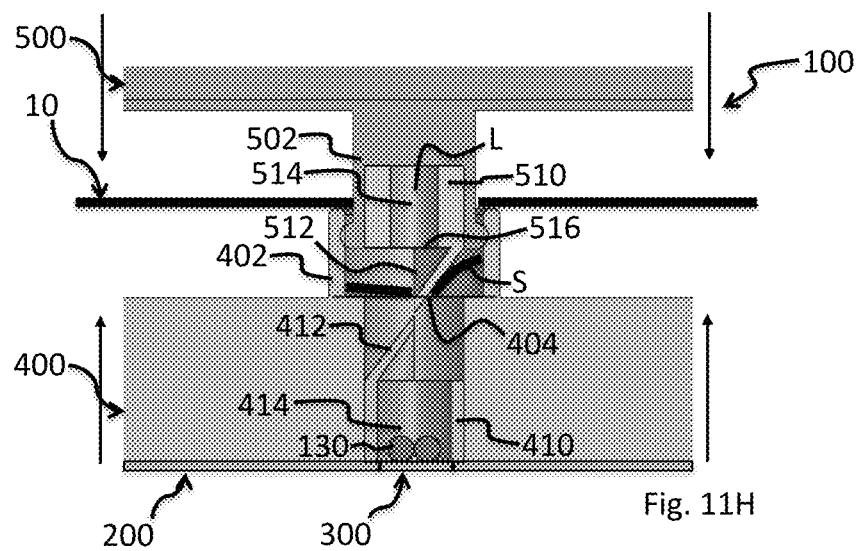
Figure 11I:
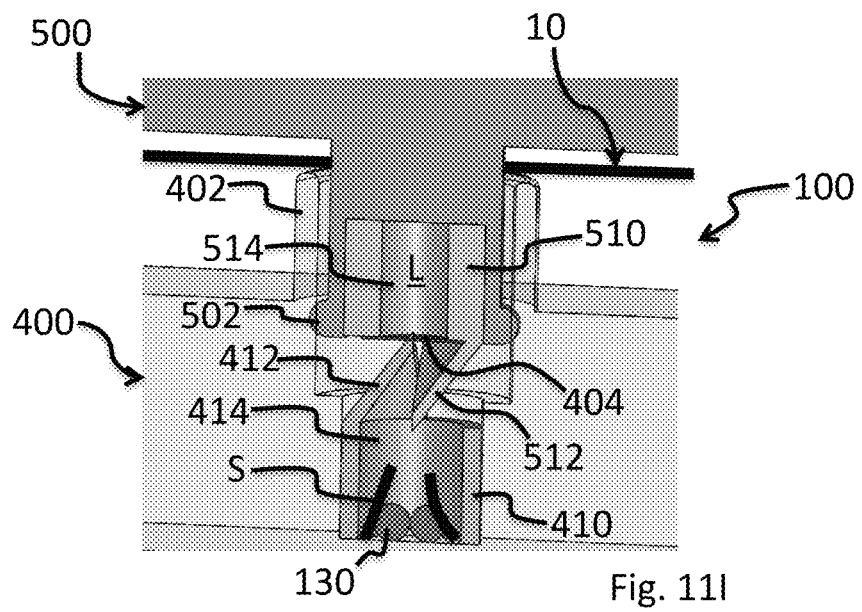
Figure 11J:
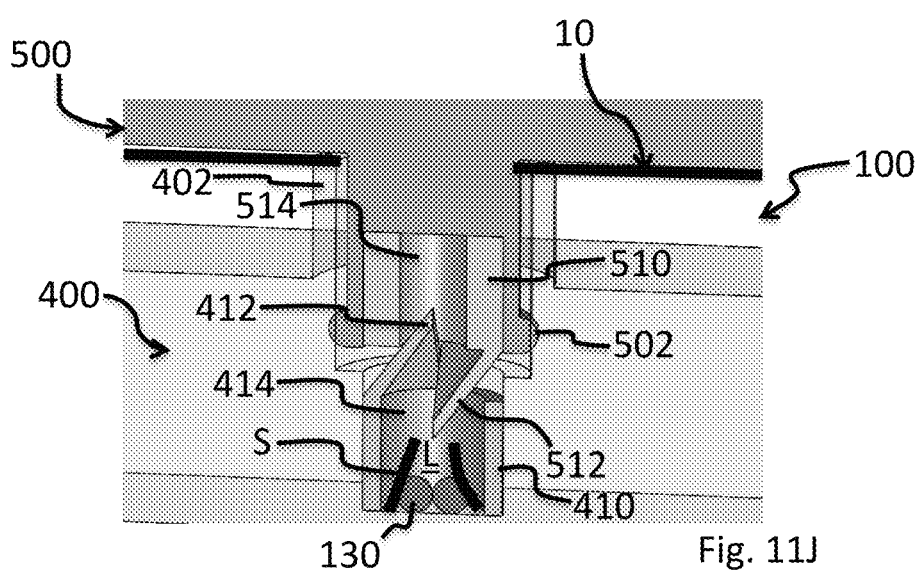

As seen in FIG. 11H, continued approximation of reaction chamber 400 and punch element 500 causes cutting element 512 of liquid insert 510 to puncture seal 404 of reaction chamber 400, thereby providing access to reagent insert 410. As seen in FIG. 11I, still further approximation causes cutting element 412 of reagent insert 410 to puncture seal 516 of liquid insert 510, thereby causing liquid L to flow out of liquid chamber 514 into reagent chamber 414. As seen in FIG. 11J, full approximation of reaction chamber 400 with punch element 500 positions all materials necessary for nucleic acid amplification and detection (sample S, reagents 130 and optional liquid L) within reagent chamber 414.

After approximating the reaction chamber and punch element, heating element 200 heats the contents of reagent chamber 414 to achieve nucleic acid amplification of a target nucleic acid sequence of interest when present in sample S. Detection may be achieved via the naked eye and/or via sensor 300.

Apparatus 100 of FIGS. 11 optionally may be used as part of instrument 40 previously described in co-pending U.S. patent application Ser. No. 13/447,218, filed Apr. 14, 2012, which is incorporated herein by reference in its entirety. Specifically, reaction chambers 400 and punch elements 500 of apparatus 100 in FIGS. 10 may be substituted for punch elements 90 and chambers 70 of instrument 40 shown in the '218 application.

The methods and apparatus of FIGS. 1-11 provide fully contained, sample-to-answer, nucleic acid sample preparation, (optionally multiplexed) target amplification and detection in (optionally disposable, e.g., single-use disposable) apparatus that is appropriate for use in limited resource settings at the point of care by relatively unskilled users.

CONCLUSION

Although preferred illustrative embodiments of the present invention are described above, it will be apparent to those skilled in the art that various changes and modifications may be made thereto without departing from the invention. For example, while mating of various components of the apparatus has been described as mating via luer lock connections, it should be understood that luer slip, press fit or other mating connectors, per se known, may be utilized. Furthermore, while some of the described embodiments of the apparatus illustratively have utilized one or more syringes to transfer sample S to the nucleic acid amplification and detection apparatus, it should be understood that any alternative sample transfer device may be utilized, including purpose-built transfer devices.

Further still, although apparatus 100 and associated methods have been described with respect to nucleic acid amplification and detection, it should be understood that the apparatus and associated methods alternatively may comprise and/or be used for holding and analyzing a sample without necessarily amplifying and/or detecting nucleic acid in the sample. In such an embodiment, apparatus 100 may comprise sample holder 100 that maintains a nucleic acid or other sample for analysis within the reaction chamber(s), which may serve as observation and/or analysis chamber(s). Analysis may comprise, for example, one or more techniques such as microscopy, hybridization and/or protein analysis—in addition, or as an alternative, to nucleic acid amplification and detection.

When apparatus 100 comprises a sample holder, a method of holding a sample for analysis may comprise collecting a sample matrix, transferring the sample matrix through at least one microfluidic channel to at least one reaction/observation/analysis chamber, optionally heating the sample matrix as part of an analytical technique, and preventing backflow of the sample matrix from the at least one chamber through the at least one microfluidic channel (e.g., during heating). Backflow prevention may prevent cross-contamination when multiple chambers are provided. Backflow prevention may be achieved via a one-way valve into the reaction/observation/analysis chamber(s) and/or via blocking of the microfluidic channel(s) after transferring of the sample matrix to the chamber(s).

It is intended in the appended claims to cover all such changes and modifications that fall within the true spirit and scope of the invention.

What is claimed is:

1. A method for amplification and detection of a target nucleic acid sequence in a sample, the method comprising: transferring the sample through an inlet into a diagnostic apparatus; distributing the sample among a plurality of microfluidic channels of the diagnostic apparatus, each microfluidic channel extending to one of a plurality of reaction chambers in the diagnostic apparatus, at least one of the reaction chambers having a nucleic acid amplification reagent therein, so that a portion of the sample is received in each reaction chamber; heating the reaction chambers in order to amplify any target nucleic acid sequence within the sample portion; manually sliding a locking valve within a void of the diagnostic apparatus from an open position to a closed position after the transferring step to block all of the microfluidic channels and prevent backflow of the sample portion from each reaction chamber through the microfluidic channel extending to it during heating; and detecting in the at least one reaction chamber amplification of the target nucleic acid sequence within the sample.

2. The method of claim 1, further comprising venting overflow from the reaction chambers.

3. The method of claim 2, wherein venting overflow further comprises venting to at least one sequestered overflow chamber.

4. The method of claim 2, wherein venting overflow further comprises venting gases through flow control media while precluding venting of fluids.

5. The method of claim 2, wherein venting comprising moving air from the reaction chambers through a medium that permits the passage of air but not fluid.

6. The method of claim 1, further comprising disposing of the diagnostic apparatus and sample after one-time use.

7. The method of claim 1, wherein heating further comprises: heating the reaction chambers with a heating element; and disposing of the heating element after one-time use.

8. The method of claim 1, wherein detecting amplification further comprises detecting a color shift in a colorimetric dye, detecting an increase in turbidity, or detecting fluorescence.

9. The method of claim 1, wherein distributing further comprises transferring the sample through at least one branching microfluidic channel that distributes the sample matrix across the reaction chambers.

10. The method of claim 1, wherein preventing backflow further comprises preventing cross-contamination between the plurality of reaction chambers.

11. The method of claim 1, further comprising amplifying and detecting different target nucleic acid sequences in different reaction chambers.

12. The method of claim 1, further comprising collecting the sample with a sample collector.

13. The method of claim 12, further comprising eluting the sample from the sample collector.

14. The method of claim 13, wherein eluting comprises depressing a plunger of a syringe.

15. The method of claim 14, further comprising connecting the syringe and sample collector to the diagnostic apparatus prior to the step of depressing the plunger.

16. The method of claim 1, wherein a first reaction chamber of the plurality of reaction chambers contains a first nucleic acid amplification reagent therein and a second reaction chamber of the plurality of reaction chambers contains a second nucleic acid amplification reagent different from the first nucleic acid amplification reagent.

17. The method of claim 1, wherein at least one reaction chamber of the plurality of reaction chambers contains a quantity of the target nucleic acid sequence prior to the step of transferring the sample through the inlet into the diagnostic apparatus.

18. The method of claim 1, wherein the diagnostic apparatus further comprises at least one additional reaction chamber not connected to any of the plurality of microfluidic channels, the additional reaction chamber containing a nucleic acid amplification reagent.

19. The method of claim 1, wherein the locking valve comprises a plurality of lumens, each microfluidic channel aligning with one of the lumens when the valve is in an open position, the sliding step comprising sliding the locking valve to a closed position in which the microfluidic channels are not aligned with the lumens.

20. The method of claim 1, wherein each of the reaction chambers has a volume of less than 100 microliters.

21. The method of claim 1, wherein the detecting step comprises viewing the reaction chambers through a transparent cover.

22. The method of claim 1, wherein the sample is not lysed with lysing chemicals prior to the transferring step.

* * * * *